United States Patent [19]

Williams

[11] Patent Number: 5,487,578
[45] Date of Patent: Jan. 30, 1996

[54] TWEEZER APPARATUS FOR USE IN MAKING STUFFED ARTICLES

[76] Inventor: Charlotte I. Williams, 3653 Jacob Rd., Grass Lake, Mich. 49240

[21] Appl. No.: 432,684

[22] Filed: May 2, 1995

[51] Int. Cl.⁶ .............................. A61B 17/30; B25B 9/02
[52] U.S. Cl. .......................................................... 294/99.2
[58] Field of Search ................................. 294/8.5, 11, 16, 294/33, 99.2, 106, 118, 902; 29/270, 278, 805; 81/487, 488; 606/205, 207, 210

[56] References Cited

U.S. PATENT DOCUMENTS

| | | | |
|---|---|---|---|
| 3,653,389 | 4/1972 | Shannon | 294/99.2 X |
| 4,044,771 | 8/1977 | Wannag | 294/99.2 X |
| 4,250,608 | 2/1981 | Mulkey | 294/99.2 X |
| 4,424,998 | 1/1984 | Lile | 294/118 |

*Primary Examiner*—Johnny D. Cherry
*Attorney, Agent, or Firm*—Harness, Dickey & Pierce

[57] ABSTRACT

Tweezer apparatus for us in the making of stuffed articles. The apparatus comprises an elongated body member having a pair of generally parallel leg members that are cantilever supported so that they can be moved toward and away from each other to enable the tip ends of the leg members to grasp and then release stuffing material. The tip of one leg member is pointed so that it can be used to poke stuffing into niches in stuffed objects. The tip end of the other leg member terminates in a blunt surface to enable use of this leg member to pack stuffing into objects to be stuffed.

4 Claims, 1 Drawing Sheet

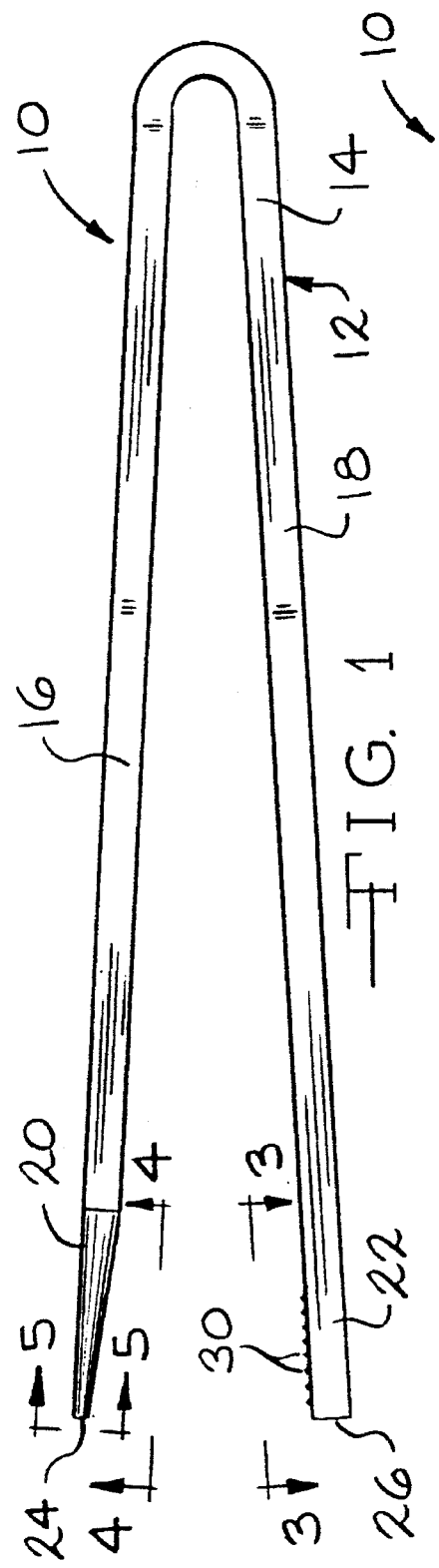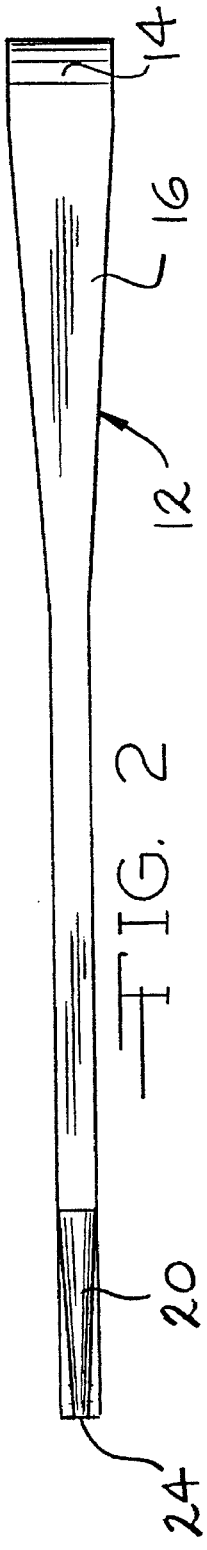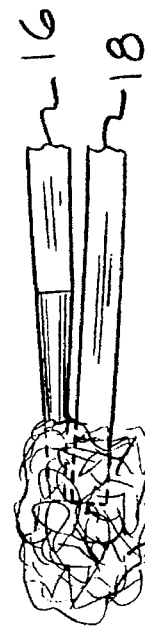

TWEEZER APPARATUS FOR USE IN MAKING STUFFED ARTICLES

BACKGROUND AND SUMMARY OF THE INVENTION

The present invention relates generally to the field of stuffed articles such as animals, pillows, toys and the like which consist of an outer hollow member formed of a flexible material such as cloth, leather, plastic or the like and an internal packing such as cotton or wool, batting or stuffing. More particularly, this invention relates to tweezer apparatus which is operable by an artist, craftsman, or the like to push the batting or stuffing into desired niches, crevices or corners of the stuffed article and pack the stuffing or batting to the desired density in the desired places within the stuffed article.

The tweezer apparatus of this invention thus facilitates the efficient manufacture of stuffed articles and enables the manufacture of stuffed articles of improved quality.

The stuffing tweezer apparatus of this invention comprises an elongated body member having a handle portion at one end and a pair of generally parallel leg members extending from the handle portions. The leg members are integral with the handle portion and each of the legs is cantilever supported on the handle portion so that they extend away from the handle portion in a spaced relation. The legs terminate in free working ends, one of which is of a tapered shape and the other of which terminates in a blunt surface.

The tapered shape terminates in a point and facilitates the packing of the stuffing into niches in the stuffed article. The remaining leg member with the blunt surface is operable either in cooperation with the pointed leg member, when the legs are squeezed together, or the leg member that terminates in the blunt surface can be used by itself for the purpose of packing stuffing to a desired density.

The leg members are deflectable toward and away from each other to enable use of the leg members to trap stuffing in desired quantities between the tip ends of the leg members when the tip ends are moved toward each other. The trapped stuffing is releasable from a clamped position between the working ends of the leg members when the leg members are released for movement away from each other to move the working ends into spaced positions thereby enabling accurate placing of the stuffing into an object being stuffed.

The elongated body member of this invention is preferably formed of a resilient plastic material which can readily be molded in the desired shape to provide for an integral one-piece body member.

The leg members are long and relatively thin and are spaced apart in an amount equal to two to three times the combined widths of the leg members. This configuration enables the body member to be quickly manipulated by dexterous fingers so as to quickly transfer stuffing or batting from a bulk source to the inside of an article to be stuffed. Furthermore, the leg members can be easily and quickly manipulated by the fingers so as to place and push the stuffing into the desired crevices and niches in the object being stuffed. The leg members are also readily manipulated so as to pack the stuffing to a desired density.

Further objects, features and advantages of the invention will become apparent from a consideration of the following description when taken in connection with the accompanying drawing.

BRIEF DESCRIPTION OF THE DRAWING

FIG. 1 is a side view of the stuffing tweezer apparatus of this invention showing the leg members in the tweezer apparatus in a normal spaced relation;

FIG. 2 is a top view of the tweezer apparatus of this invention;

FIGS. 3 & 4 are fragmentary elevational views of the tip ends of the leg members as seen from substantially the arrows 3—3 and 4—4, respectively, in FIG. 1;

FIG. 5 is an end view of one of the leg members; and

FIG. 6 is a fragmentary view of the tweezer apparatus showing the leg members deflected toward each other so as to grasp a quantity of stuffing at least partially between the tip ends of the leg members.

DETAILED DESCRIPTION OF THE DRAWING

With reference to the drawing, the tweezer apparatus of this invention, indicated generally at 10, is illustrated in FIG. 1 as comprising a unitary one-piece body member 12 of elongated shape having a handle portion 14 at one end. A pair of leg members 16 and 18 emanate from the handle portion 14 and extend in a generally diverging relation away from the handle portion 14.

The leg members 16 and 18 are integral with the handle portion 14 and are cantilever supported at their inner ends on the handle portion 14. At their opposite ends, the leg members 16 and 18 terminate in free working ends 20 and 22, respectively. The working end 20 of the leg member 16 is of a tapered shape and terminates at its tip end in a dull point 24 thereby enabling use of the working end 20 to poke stuffing into niches and crevices in stuffed objects.

The working end 22 of the other one of the leg members 18 terminates at its tip end in a squared off or blunt surface 26 to enable use of the working end 22 to pack stuffing into objects to be stuffed. A plurality of ridges 30 on the inner side of the working end 22 facilitates the grasping of stuffing between the legs 16 and 18. The leg members 16 and 18 are deflectable toward and away from each other to enable use of the leg members 16 and 18 to trap stuffing, indicated at 28 in FIG. 2, in desired quantities between the tip ends 20 and 22 of the leg members 16 and 18 when the tip ends are moved toward each other. The trapped stuffing 28 is releasable from a clamped position between the working ends 20 and 22 of the leg members 16 and 18 when the leg members are released so that they can move away from each other to the spaced position shown in FIG. 1. This enables accurate placing of the stuffing into an object being stuffed.

In the use of the apparatus 10, the artist or crafts-person grasps the handle portion 14 in one hand and, with the thumb and forefinger, manipulates the leg members 16 and 18 so as to move them toward each other to pick up a desired amount of stuffing 28 as shown in FIG. 6. The working end 22 of the leg 18 is formed with a section 32 of increased width to prevent the leg 16 from sliding off one side of the leg 18 when the legs 16 and 18 are moved into engagement to grab stuffing 28.

The apparatus 10, with the stuffing grasped between the legs 16 and 18, is then manually manipulated to place the stuffing 28 at the desired position within the object being stuffed, following which, the leg members 16 and 18 are released so that the stuffing 28 is released from a held position between the leg members 16 and 18. The body member 12 can then be manipulated so as to use the tip end 20 of the leg member 16 to push the stuffing 28 into niches in the object being stuffed. Similarly, the body member 12 can be manipulated to use the engaged ends 24 and 26 with the leg members 16 and 18 in the position shown in FIG. 2 to pack the stuffing 28 in the object being stuffed to a desired density. If desired, only the leg 18 can be used for this packing step.

From the above description it is seen that this invention provides improved tweezer apparatus 10 which is operable to facilitate and improve the effectiveness of stuffing an article to be stuffed.

I claim:

1. Stuffing tweezer apparatus comprising an elongated body member having a handle portion at one end and a pair of generally diverging leg members each having a pair of ends, one of said ends of each of said leg members being integral with said handle portion, each of said leg members being cantilever supported at said one end on said handle portion and terminating in a free working end spaced from said handle portion, the working end of one of said leg members being of a tapered shape and terminating in a point thereby enabling use of the working end of said one leg member to poke stuffing into niches in stuffed objects, the working end of the other one of said leg members terminating in a blunt surface to enable use of said working end of said other one of said leg members to pack stuffing into objects to be stuffed, said leg members being deflectable toward and away from each other to enable use of said leg members to trap stuffing in desired quantities between the tip ends of said leg members when said tip ends are moved toward each other, said trapped stuffing being releasable from a clamped position between the working ends of said leg members when said leg members move away from each other to move said working ends into spaced positions thereby enabling accurate placing of said stuffing into an object being stuffed.

2. Stuffing tweezer apparatus according to claim 1 wherein said elongated body is capable of being used to poke stuffing in a position of said leg members in which said working ends are engaged with each other.

3. Stuffing tweezer apparatus according to claim 1 wherein said body member is a one-piece member formed of a moldable plastic material which in the final form of said body is a resilient material.

4. Stuffing tweezer apparatus according to claim 3 further including a wide section adjacent one of said tip ends.

* * * * *